United States Patent [19]

Onoue et al.

[11] Patent Number: 4,713,461
[45] Date of Patent: Dec. 15, 1987

[54] PROCESS FOR PRODUCING GLUTACONIC ACID DERIVATIVES

[75] Inventors: Hiroshi Onoue, Nara; Hiromi Takahashi, Hyogo, both of Japan

[73] Assignee: Shionogi & Co., Ltd., Osaka, Japan

[21] Appl. No.: 763,784

[22] Filed: Aug. 8, 1985

[30] Foreign Application Priority Data

Aug. 24, 1984 [JP] Japan .................. 59-176954

[51] Int. Cl.$^4$ .................. C07D 277/38; C07D 277/46
[52] U.S. Cl. .................. 548/194; 548/195
[58] Field of Search .................. 548/194, 195

[56] References Cited

FOREIGN PATENT DOCUMENTS 0168025 1/1986 European Pat. Off. ............ 548/195
60-34957 2/1985 Japan .................. 548/194

OTHER PUBLICATIONS

Morrison and Boyd, "Organic Chemistry", Third Edition, Allyn and Bacon, Inc., © 1973, pp. 873–874.

Primary Examiner—Robert Gerstl
Attorney, Agent, or Firm—Wenderoth, Lind & Ponack

[57] ABSTRACT

A useful intermediate, glutaconic acid ester derivative (III), is prepared by Michael-type condensation of thiazoleacetic acid derivative (I) with alkoxyacrylic acid derivative (II) in the presence of base.

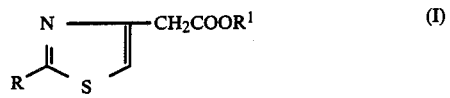

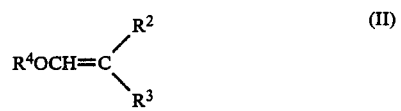

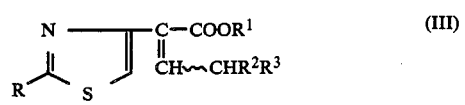

(wherein,
R is amino or protected amino;
$R^1$ is an ester forming group;
$R^2$ is hydrogen, cyano, or esterified carboxy;
$R^3$ is hydrogen, cyano, or esterified carboxy; and
$R^4$ is lower alkyl or aralkyl).

7 Claims, No Drawings

PROCESS FOR PRODUCING GLUTACONIC ACID DERIVATIVES

This invention relates to glutaconic acid derivatives useful as starting materials for producing e.g., anti-bacterials. More specifically, it relates to a process for producing glutaconic acid derivatives (III) by a Michael type condensation of thiazoleacetic acid derivative (I) and alkoxyacrylic acid derivative (II) in the presence of base.

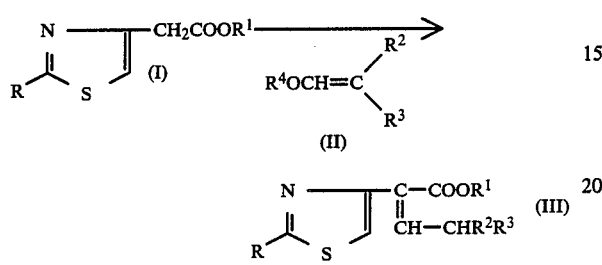

(wherein,
R is amino or protected amino;
$R^1$ is an ester forming group;
$R^2$ is hydrogen, cyano, or esterified carboxy;
$R^3$ is hydrogen, cyano, or esterified carboxy; and
$R^4$ is lower alkyl or aralkyl).

The groups in the preceding formulas are explained below.

In the protected amino R, representative amino-protecting groups are 1C to 5C alkanoyl (e.g., formyl, acetyl, isobutyryl), halo-1 to 5C alkanoyl (e.g., chloroacetyl), 2C to 6C alkoxyformyl (e.g., methoxycarbonyl, t-butoxycarbonyl, trichloroethoxycarbonyl, iodoethoxycarbonyl), 8C to 15C aralkoxyformyl (e.g., benzyloxycarbonyl, dimethylbenzyloxycarbonyl, nitrobenzyloxycarbonyl), 1C to 15C (alkyl or aryl)-sulfonyl (e.g., methanesulfonyl, ethanesulfonyl, benzenesulfonyl, toluenesulfonyl, bromobenzenesulfonyl), and other acyls or 19 to 20C triarylmethyl (e.g., triphenylmethyl), 3C to 10C enamine forming group, tri-(1C to 5C)-alkylsilyl (e.g., tert-butyldimethylsilyl, trimethylsilyl), 2C to 10C Schiff base-forming groups (e.g., dimethylaminomethylidene, benzylidene), and other amino-protecting groups.

The ester-forming group $R^1$, $R^5$ and the protective group in the esterified carboxys $R^2$ and $R^3$ can each be, for example, 1C to 8C alkyl (e.g., methyl, ethyl, propyl, isopropyl, butyl, t-butyl), 1C to 5C alkyl substituted by halogen, 1C to 5C alkoxy, 1C to 8C sulfonyl (e.g., chloromethyl, trichloromethyl, methoxyethyl, methanesulfonylethyl), 2C to 5C alkenyl (e.g., vinyl, propenyl, prenyl), 7C to 15C aralkyl (e.g., benzyl, methylbenzyl, nitrobenzyl, methoxybenzyl, diphenylmethyl), or other conventional carboxy-protecting groups.

The lower alkyl $R^4$ can be 1C to 5C alkyl (e.g., methyl, ethyl, propyl, butyl, isobutyl, especially methyl and ethyl). Preferable aralkyls $R^4$ can be 7C to 15C aralkyl (e.g., benzyl, methylbenzyl).

The Michael-type reaction of this invention consists of the following steps: i.e., the reaction of thiazoleacetic acid derivative (I) with the base to convert active methylene into carbanion (Ia), the Michael addition of this anion to alkoxyacrylic acid derivative (II) giving an intermediate, alkoxyglutaric acid derivative (Ib), and the elimination of alcohol $R^4OH$ from the latter to give glutaconic acid derivative (III).

The said carbanion formation, addition, and alcohol-elimination each may proceed in the presence of the base under anhydrous condition. So, the isolation of intermediates (Ia) or (Ib) is not always necessary. Thus, thiazoleacetic acid derivative (I) is reacted with alkoxyacrylic acid derivative (II, especially when $R^3$ is hydrogen) to give objective glutaconic acid derivative (III).

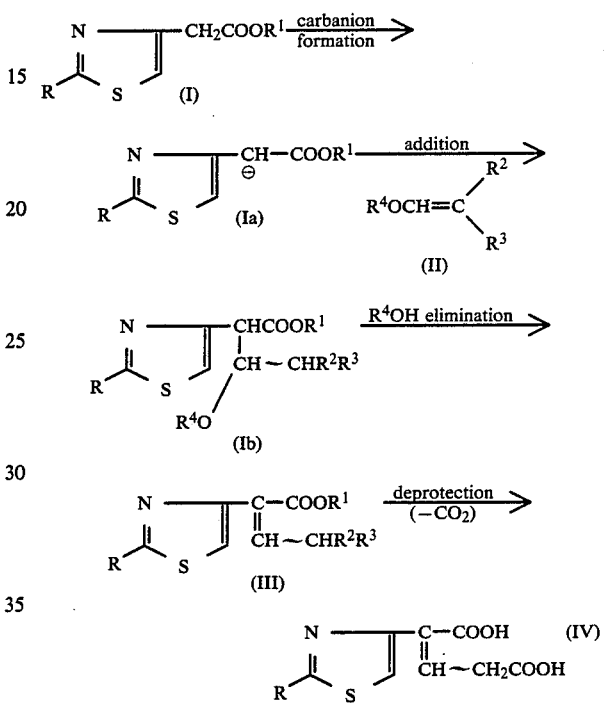

Glutaconic acid ester derivatives (III) can be deesterified (by e.g., hydrolysis), giving glutaconic acid derivatives (IV) (when $R^2$ and $R^3$ are both carboxy, followed by decarboxylation) which are useful for producing penicillins and cephalosporins.

The base for the reactions can be a metal compound e.g., hydride or alkoxide of alkali metal.

The carbanion-formation and addition are carried out under dry condition.

The addition proceeds well by contacting alkoxyacrylic acid derivative (II) (preferably 1 to 5 equivalents, especially 1 to 3 equivalents) with the carbanion formed in the preceding step. Addition product (Ib) can sometimes be isolated from the reaction mixture in a conventional way.

The elimination of alcohol $R^4OH$ proceeds by the action of a base. This reaction can proceed rapidly also in a polar solvent (e.g., water).

Thus produced glutaconic acid derivative (III) is usually a mixture of geometrical isomers in relation to the double bond. The over-all yield from thiazoleacetic acid derivative (I) may amount up to over 90%.

Deprotection of this (by e.g., hydrolysis) gives glutaconic acid derivative (IV). When $R^2$ and $R^3$ in glutaconic acid ester (III) are both esterified carboxy, decarboxylation occurs simultaneously with the deprotection giving the same glutaconic acid derivative (IV).

The above steps proceed well in a solvent. Such solvent can be ether (e.g., dimethoxyethane, tetrahydrofuran, dioxane), nitrile (e.g., acetonitrile, propionitrile, benzonitrile), sulfoxide (e.g., dimethylsulfoxide), amide (e.g., N,N-dimethylformamide, N,N-dimethylacetamide, hexamethylphosphorotriamide), ester (e.g., methyl formate, ethyl acetate), or a mixture of these. Acrylic acid derivative (II) can serve as a solvent. The reaction is usually carried out well at −30° to 100° C. (especially −20° to 70° C.) often for 5 minutes to 10 hours.

The starting thiazoleacetic acid derivative (I) and alkoxyacrylic acid derivative (II) are known compounds or easily available from known compounds. The intermediates (i.e., alkoxyglutaric acid derivative (Ib), glutaconic acid ester derivative (III), and glutaconic acid derivative (IV)) are all novel compounds.

The following examples illustrate this invention.

In the examples, "part" shows part by weight and "equivalent" shows molar equivalent.

(Abbreviations)
BOC=t-butoxycarbonyl;
Cbz=benzyloxycarbonyl;
DMA=dimethylacetamide;
Et=ethyl;
nd=not determined;
rt=room temperature; and
Bzl=benzyl;
DBU=diazabicycloundecene;
DMF=dimethylformamide;
Me=methyl;
Ph=phenyl;
THF=tetrahydrofuran.

EXAMPLE 1

(Addition)

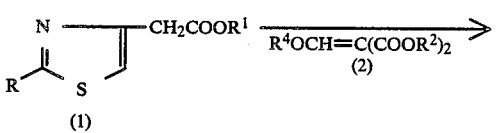

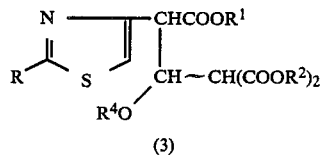

To a suspension of sodium hydride in tetrahydrofuran is added a solution of thiazoleacetic acid ester (1) and 2-(alkoxymethylidene)malonic acid ester (2) in tetrahydrofuran. After stirring at the listed temperature for listed time, the mixture is diluted with ethyl acetate, neutralized with acetic acid, washed with water, dried, and concentrated in vacuo. The residue gives, if required after purifying by chromatography, alkoxyglutaric acid ester (3). Geometric isomers can be isolated.

The reaction conditions are listed on Table 1 and the physical constants of the products are listed on Table 5.

EXAMPLE 2

(Elimination)

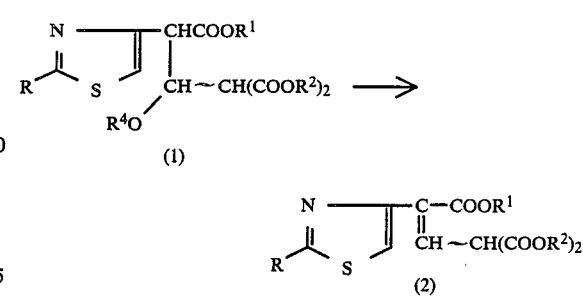

To a solution of alkoxyglutaric acid derivative (1) in a solvent is added the given base. After the mixture is stirred at given temperature for given time, the mixture is neutralized, diluted with water and ethyl acetate, washed with water, dried, and concentrated in vacuo. The residue gives, if required after purifying by silica gel chromatography, carboxyglutaconic acid ester derivative (2). Geometric isomers can be isolated.

The reaction conditions are listed on Table 2 and the physical constants of the products are listed on Table 6.

EXAMPLE 3

(Hydrolysis and decarboxylation)

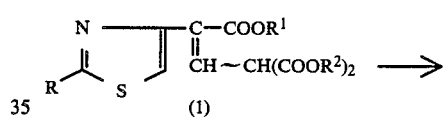

To a solution of carboxyglutaconic acid ester (1) in given solvent is added given base. After stirring at given temperature for given time, the mixture is diluted with water and ethyl acetate. The separated aqueous layer is acidified with hydrochloric acid and extracted with ethyl acetate. The extract is washed with water, dried, and concentrated in vacuo. The residue is glutaconic acid derivative (2).

The reaction conditions are listed on Table 3 and the physical constants of the products are listed on Table 7.

EXAMPLE 4

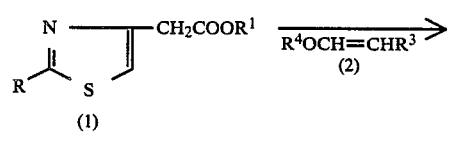

A solution of base, alkoxyacrylic acid derivative reagent (2) and thiazoleacetic acid derivative (1) in N,N-dimethylformamide is kept at given temperature for given time. The reaction mixture is poured onto a mixture of 5% hydrochloric acid and ethyl acetate. The organic layer is taken, washed with water, dried, and concentrated in vacuo to give glutaconic acid ester derivative (3), if required after purifying by chromatography.

When the base is a hydride, a trace amount of alcohol can be added as a reaction initiator.

The reaction conditions are listed on Table 4 (Part 1) and the physical constants of the products are listed on Table 8.

EXAMPLE 5

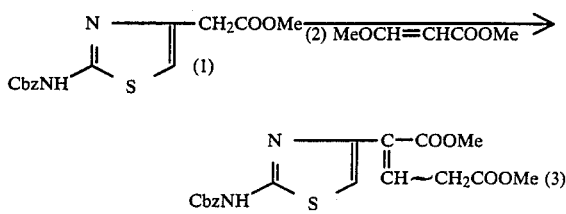

To a solution of 2-(2-benzyloxycarbonylamino-4-thiazolyl)acetic acid methyl ester (1) in the listed solvent are added 3-methoxyacrylic acid methyl ester reagent (2) and sodium methoxide. After reacting at 0° to 15° C. for 15 minutes, the mixture is analyzed by the high performance liquid chromatography to determine the yield of 2-(2-benzyloxycarbonylamino-4-thiazolyl)-glutaconic acid dimethyl ester (3).

The reaction conditions and yields are listed on Table 4 (Part 2).

PREPARATION 1

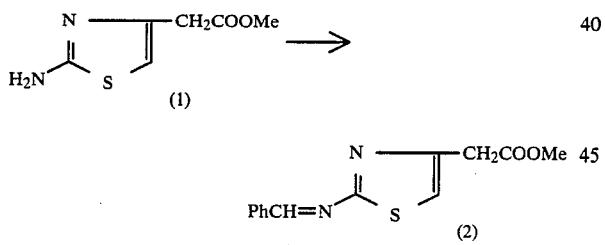

To a solution of amine (1) in toluene (4.3 parts) is added benzaldehyde (5 equivalents). After refluxing under azeotropic condition for 2 hours, the mixture is concentrated to remove the solvent and benzaldehyde. The residue is purified by silica gel chromatography (hexane:acetone=3:2) to give Schiff base (2). mp. 71°-72° C. (hexane-ether). Yield: 62.8%.

IR(Nujol)$\nu$: 1730, 1605, 1585, 1160 cm$^{-1}$.

NMR(CDCl$_3$)$\delta$: 3.71(s, 3H), 3.80(s, 2H), 7.07(s, 1H), 7.47(m, 3H), 7.93 (m, 2H), 8.98(s, 1H) ppm.

PREPARATION 2

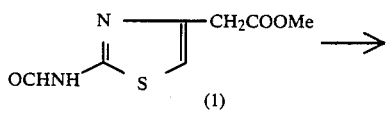

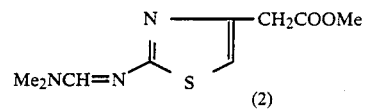

Phosphorus oxychloride (5 equivalents) is added to N,N-dimethylformamide (1.8 parts) at 6° to 11° C. for 18 minutes and the mixture is diluted with chloroform (4.5 parts). The solution is added to a suspension of N-formyl compound (1) in chloroform (10 parts) at 7° C. during 15 minutes. The mixture is stirred at room temperature for 140 minutes. The reaction mixture is cooled to 5° C., neutralized with aqueous 3N-sodium hydroxide to pH 7, and extracted with chloroform. The extract is washed with water, dried, and concentrated in vacuo. The residue is purified by silica gel chromatography (ethyl acetate:acetonitrile=8:2) to give carbodiimide (2). Yield: 58.2%.

IR(CHCl$_3$)$\nu$: 1730, 1630, 1100 cm$^{-1}$.

NMR(CDCl$_3$)$\delta$: 3.03, 3.06(2×s, 6H), 3.70(s, 5H), 6.60(s, 1H), 8.17(s, 1H) ppm.

PREPARATION 3

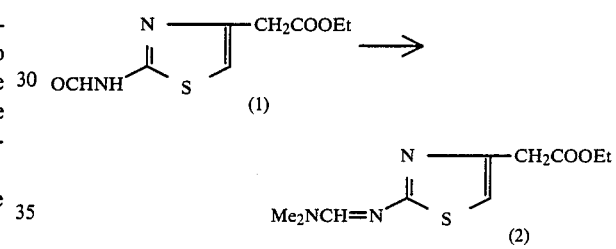

N-Formyl compound (1) is treated in the same manner with that of Preparation 2 giving carbodiimide (2). Yield: 87.7%.

IR(CHCl$_3$)$\nu$: 1730, 1620, 1103 cm$^{-1}$.

NMR(CHCl$_3$)$\delta$: 1.26(t, J=7 Hz, 3H), 3.04(s, 6H), 3.63(s, 2H), 4.15(q, J=7 Hz, 2H), 6.60(s, 1H), 8.14(s, 1H) ppm.

PREPARATION 4

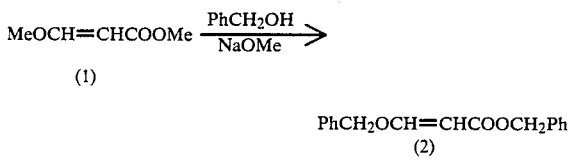

A mixture of 3-methoxyacrylic acid methyl ester (1), benzyl alcohol (1.2 equivalents), a solution of sodium methoxide in methanol (0.05 equivalents), and toluene (3.7 parts) is heated for 3 hours to remove methanol under azeotropic distillation. The mixture is concentrated in vacuo to remove the solvent, distilled in vacuo to remove by-products (94° to 112° C. at 3 mmHg), and cooled. The residue is chromatographed over silica gel (benzene:ethyl acetate=95:5) to give 3-benzyloxyacrylic acid benzyl ester (2). Yield: 45%.

NMR(CDCl$_3$)$\delta$: 4.74(s, 2H), 5.11(s, 2H), 5.32(d, J=13 Hz, 1H), 7.29(m, 10H), 7.69(d, J=13 Hz, 1H) ppm.

TABLE 1

(Addition)

$$\underset{(1)}{\underset{R}{\overset{N}{\diagdown}}\underset{S}{\diagup}}\text{—CH}_2\text{COOR}^1 \xrightarrow{R^4OCH=C(COOR^2)_2 \atop (2)} \underset{(3)}{\underset{R}{\overset{N}{\diagdown}}\underset{S}{\diagup}}\begin{array}{c}\text{CHCOOR}^1\\|\\ \text{CH—CH(COOR}^2)_2\\ {}^{/}\\ R^4O\end{array}$$

| No. | R | R¹ | R² | R⁴ | NaH (equiv.) | THF (part) | reagent (equiv.) | THF (part) | temp (°C.) | time (min) | yield (%) | stereoisomers A (isolated) B |
|---|---|---|---|---|---|---|---|---|---|---|---|---|
| 1 | BOCNH | Me | Et | Et | 2.0 | 5.7 | 1.2 | 5.7 | 20 | 210 | 52.7 | 21.9    30.8 |
| 2 | CbzNH | Me | Me | Me | 2.3 | 4.8 | 1.6 | 9.7 | 10<br>rt | 10<br>180 | 84 | mixture |
| 3 | CbzNH | Me | Et | Et | 2.2 | 5.8 | 1.4 | 5.8 | rt<br>40<br>rt | 15<br>30<br>150 | 31.7 | 11.5    20.2 |
| 4 | OCHNH | Et | Et | Et | 2.0 | 20.5 | 1.2 | — | rt | 120 | 60 | 4:5 mixture |
| 5 | PhCH=N | Me | Et | Et | 2.0 | 8.9 | 2.0 | 7.1 | 8<br>rt<br>60 | 10<br>210<br>60 | 40 | |
| 6 | Me₂NCH=N | Me | Me | Me | 3.0 | 8.8 | 1.5 | 6.1 | 3<br>rt<br>60 | 7<br>60<br>45 | >85 | continued to Table 2, No. 7. |
| 7 | Me₂NCH=N | Et | Et | Et | 3.0 | 8.6 | 1.5 | 86.3 | rt<br>60 | 120<br>40 | >60 | continued to Table 2, No. 8. |

TABLE 2

(Elimination)

$$\underset{(1)}{\underset{R}{\overset{N}{\diagdown}}\underset{S}{\diagup}}\begin{array}{c}\text{CHCOOR}^1\\|\\ \text{CH—CH(COOR}^2)_2\\ {}^{/}\\ R^4O\end{array} \longrightarrow \underset{(2)}{\underset{R}{\overset{N}{\diagdown}}\underset{S}{\diagup}}\begin{array}{c}\text{C—COOR}^1\\||\\ \text{CH—CH(COOR}^2)_2\end{array}$$

| No. | R | R¹ | R² | R⁴ | solvent (part) | base (equiv.) | temp (°C.) | time (min) | yield (%) | cis:trans |
|---|---|---|---|---|---|---|---|---|---|---|
| 1 | BOCNH | Me | Et | Et | MeOH 3.6 | 2N—KOH 4.0 | 0 | 15 | 86 | 3:4 (from isomer A) |
| 2 | BOCNH | Me | Et | Et | MeOH 3.6 | 2N—KOH 4.0 | 0 | 15 | — | 3:4 (from isomer B) |
| 3 | CbzNH | Me | Me | Me | CH₂Cl₂ 19.6 | 2N—KOH 10.0 | rt | 300 | — | continued to Table 3, No.2 |
| 4 | CbzNH | Me | Et | Et | MeOH 3.1 | 2N—KOH 4.0 | 0 | 30 | 82 | 3:5 |
| 5 | OCHNH | Et | Et | Et | EtOH 3.5 | 2N—KOH 4.0 | rt | 60 | 79 | 5:6 |
| 6 | PhCH=N | Me | Et | Et | CH₂Cl₂ 25.5 | DBU 1.2 | rt | 120 | 38 | — |
| 7 | Me₂NCH=N | Me | Me | Me | The same condition with Table 1, No. 6. | | | | 85 | (over-all yield from Table 1, No. 6) |
| 8 | Me₂NCH=N | Et | Et | Et | The same condition with Table 1, No. 7. | | | | 60 | (over-all yield from Table 1, No. 7) |

TABLE 3

(Hydrolysis + decarboxylation)

$$\underset{(1)}{\underset{R}{\overset{N}{\diagdown}}\underset{S}{\diagup}}\begin{array}{c}\text{C—COOR}^1\\||\\ \text{CH—CH(COOR}^2)_2\end{array} \longrightarrow \underset{(2)}{\underset{R}{\overset{N}{\diagdown}}\underset{S}{\diagup}}\begin{array}{c}\text{C—COOH}\\||\\ \text{CH—CH}_2\text{COOH}\end{array}$$

| No. | R | R¹ | R² | Solvent (w/w) | Base (equiv.) | temp. (°C.) | time (min) | yield (%) |
|---|---|---|---|---|---|---|---|---|
| 1 | BOCNH | Me | Et | MeOH (9.0) | 1N—NaOH (10.0) | rt | 360 | 34 |
| 2 | CbzNH | Me | Me | CH₂Cl₂ (19.6) | 2N—KOH (10.0) | rt | 300 | 57 (over-all from Table 2, No. 3) |
| 3 | CbzNH | Me | Et | MeOH (8.3) | 1N—NaOH (10.0) | rt | 300 | 26 |

TABLE 4

*(Addition + Elimination)*

(Part 1)

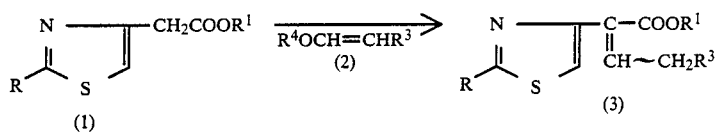

Bzl = benzyl

| No. | R | $R^1$ | $R^3$ | $R^4$ | DMF (part) | base | equiv. | $R^4OH$ (equiv.) | reagent (equiv.) | temp (°C.) | time (min) | yield (%) |
|---|---|---|---|---|---|---|---|---|---|---|---|---|
| 1 | BOCNH | Me | COOMe | Me | 6.3 | NaOMe | 3.1 | 0 | 2.4 | 0 | 40 | 60 |
| 2 | CbzNH | Me | COOMe | Me | 4.6 | NaOMe | 3.0 | 0 | 1.2 | 0 | 60 | 84 |
| 3 | CbzNH | Et | COOMe | Et | 11.8 | NaH | 2.4 | 0.2 | 1.4 | 15 | 30 | 68 |
| 4 | CbzNH | Bzl | COOBzl | Bzl | 4.1 | NaH | 3.0 | 0 | 1.6 | 10 | 60 | 46 |
| 5 | CbzNH | Bzl | COOBzl | Bzl | 4.1 | NaH | 3.0 | 0 | 1.5 | 10 | 70 | 36 |
| 6 | HCONH | Me | COOMe | Me | 18.9 | NaH | 2.5 | 2.0 | 2.0 | 0 | 30 | 78 |
| 7 | HCONH | Me | CN | Me | 18.9 | NaH | 2.5 | 1.0 | 2.0 | 0 | 40 | 42 |
| 8 | CbzNH | Me | CN | Me | 12.3 | NaH | 2.5 | 2.0 | 2.0 | 0 | 30 | 72 |
| 9 | ClCH$_2$CONH | Me | COOMe | Me | 11.8 | NaH | 2.5 | 1.0 | 2.5 | −20→0 | 60 | 60 |

(Part 2)

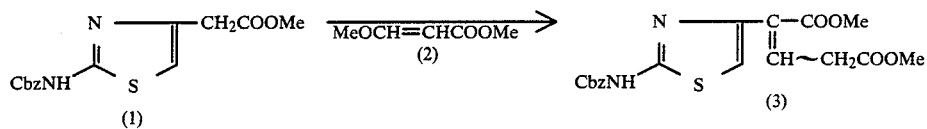

| No. | Solvent (Parts by Volume) | NaOMe (equiv.) | Reagent (2) (equiv.) | Yield (3) (%) |
|---|---|---|---|---|
| 1 | MeCN (5) | 3 | 3 | 36 |
| 2 | THF (5) | 3 | 3 | 58 |
| 3 | DMSO (5) | 2.3 | 2.3 | 69 |
| 4 | DMF (5) | 3 | 3 | 78 |
| 5 | DMA (5) | 2.5 | 2 | 67 |
| 6 | 20% HCOOMe in DMA (5) | 2.5 | 2.0 | 62 |

| Effect of temperature on Reaction No. 4 | temperature (°C.) | −20 | 4 | 18 | 33 | 42 | 58 |
|---|---|---|---|---|---|---|---|
| | yield of (3) (%) | 68.3 | 78.3 | 91.0 | 90.5 | 92.1 | 85.0 |

TABLE 5

Physical constants of 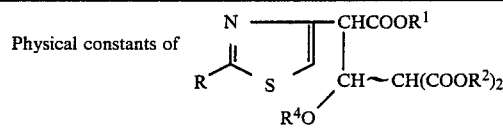

| No. | R | $R^1$ | $R^2$ | $R^4$ | IR(CHCl$_3$)$\nu$: cm$^{-1}$ | NMR(CDCl$_3$)$\delta$: ppm |
|---|---|---|---|---|---|---|
| 1A | BOCNH (Isomer A) | Me | Et | Et | nd. | 1.06(t,J = 8 Hz,3H),1.23(t,J = 8 Hz,3H),1.26(t,J = 8 Hz,3H),1.52(s,9H),3.47(d,J = 4 Hz,1H),3.69(s,3H), 3.70(m,2H),4.11(q,J = 8 Hz,2H),4.14(q,J = 8 Hz,2H), 4.24(d,J = 10 Hz,1H),4.72(dd,J$_1$ = 4 Hz,J$_2$ = 10 Hz,1H), 6.86(s,1H),8.23(s,1H). |
| 1B | BOCNH (Isomer B) | Me | Et | Et | 3410,1730. mp. 132~133° C. | 0.97(t,J = 8 Hz,3H),1.21(t,J = 8 Hz,3H),1.24(t,J = 8 Hz,3H),1.52(s,9H),3.47(m,1H),3.55(d,J = 8 Hz, 1H),3.70(s,3H),4.12(m,4H),4.27(d,J = 7 Hz,1H), 4.69(dd,J$_1$ = 7 Hz,J$_2$ = 8 Hz,1H),6.93(s,1H),8.38(s,1H). |
| 2 | CbzNH | Me | Me | Me | 3395,1734. | 3.31,3.44(2 × s,3H),3.57,3.61,3.63,3.67,3.70(5 × s,9H),3.25~3.85(m,1H),4.31~4.68(m,2H),5.28(m, 2H),6.92,6.97(2 × s,1H),7.37(s,5H),9.83(s,1H). |
| 3A | CbzNH (Isomer A) | Me | Et | Et | nd. | 1.04(t,J = 8 Hz,3H),1.18(t,J = 8 Hz,3H),1.20(t,J = 8 Hz,3H),3.48(d,J = 4 Hz,1H),3.64(s,3H),3.66(q,J = 8 Hz,2H),4.06(m,2H),4.08(q,J = 8 Hz,2H),4.35(d,J = 9 Hz,1H),4.68(dd,J$_1$ = 4 Hz,J$_2$ = 9 Hz,1H),5.26(s,2H), 6.91(s,1H),7.34(s,5H),9.47(s,1H). |
| 3B | CbzNH (Isomer B) | Me | Et | Et | nd. | 1.00(t,J = 8 Hz,3H),1.13(t,J = 8 Hz,3H),1.23(t,J = 8 Hz,3H),3.4~3.8(m,3H),3.57(s,3H),4.06(q,J = 8 Hz, 2H),4.14(q,J = 8 Hz,2H),4.45(d,J = 4 Hz,1H),4.70(dd, J$_1$ = 4 Hz,J$_2$ = 9 Hz,1H),5.22,5.36(ABq,J = 12 Hz,2H), 7.00(s,1H),7.33(s,5H),10.17(s,1H). |
| 4 | HCONH | Et | Et | Et | 3405,3180, 1732,1700. | 0.83~1.35(m,12H),3.1~3.8(m,3H),3.96~4.32(m, 7H),4.52~4.74(m,1H),6.97,7.05(2 × s,1H),8.83(s, 1H),11.77(s,1H). |
| 5 | PhCH=N | Me | Et | Et | 1730,1600, 1240. | 1.24(t,J = 7 Hz,9H),3.70(s,3H),4.14(m,6H),3.63, 4.12,(4.82(3 × m,3H),7.22,7.30(2 × s,1H),7.33(m, 2H),7.48(m,3H). |

TABLE 6

Physical constants of 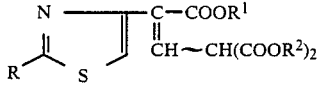

| No. | R | R¹ | R² | IR(CHCl₃)ν: cm⁻¹ | NMR(CDCl₃)δ: ppm |
|---|---|---|---|---|---|
| 1 | BOCNH | Me | Et | nd. | 1.22((t,J = 8 Hz,3H),1.24(t,J = 8 Hz,3H),1.50(s,9H), 3.80,3.84(2 × s,3H),4.17(q,J = 8 Hz,2H),4.21(q,J = 8 Hz,2H),4.84,5.13(2 × d,J = 9 Hz,J = 10Hz,1H),7.11(s, 1H),7.15(m,1H),8.65(brs,1H). |
| 2 | CbzNH | Me | Et | 3390,1724. | 1.20,1.23(2 × t,J = 8 Hz,6H),3.73,3.82(2 × s,3H), 4.16,4.20(2 × q,J = 8 Hz,4H),4.81,4.97(2 × d,J = 10 Hz,1H),5.23(s,2H),5.1∼5.4(m,7H),9.40(s,1H). |
| 3 | HCONH | Et | Et | 3390,3170, 1720. | 1.14∼1.43(m,9H),4.06∼4.44(m,6H),4.64∼4.84(d,J = 9 Hz,J = 10 Hz,1H),6.97∼7.25(m,2H),8.52,8.53(2 × s, 1H),11.27(s,1H). |
| 4 | PhCH=N | Me | Et | 1730,1600, 1240. | 1.23(t,J = 7 Hz,6H),2.6H(s,3H),4.19,4.21(q,J = 7 Hz, 4H),4.87,5.12(2 × d,J = 10 Hz,1H),7.23,7.34(2 × d,J = 10 Hz,1H),7.24,7.31(2 × s,1H),7.48,7.74(2 × m,2H). |
| 5 | Me₂NCH=N | Me | Me | 1755,1715, 1610,1165. (Nujol) mp. 88∼89° C. | 3.06(s,3H),3.12(s,3H),3.74(s,6H),3.81(s,3H), 4.82,5.27(2 × d,J = 10 Hz,1H),6.94,7.00(2 × s,1H), 7.15,7.23(2 × d,J = 10 Hz,1H),8.24,8.41(2 × s,1H). |
| 6 | Me₂NCH=N | Et | Et | 1725,1615. | 1.24,1.26(2 × t,J = 7 Hz,9H),3.06,3.10(2 × s,6H),4.18 (q,J = 7 Hz,6H),4.77,5.17(2 × d,J = 10 Hz,1H),7.03, 7.20(2 × d,J = 10 Hz,1H),7.14(s,1H),8.23,8.41(2 × s,1H). |

TABLE 7

Physical constants of 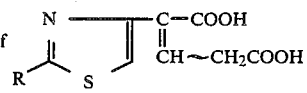

| No. | R | IR(Nujol)ν:cm⁻¹ | NMR δ:ppm |
|---|---|---|---|
| 1 | BOCNH— (cis) | 3120,1700, 1675. dp 153∼154° C. | 1.50(s,9H),3.45(d,J = 7.5 Hz,2H),7.00(t,J = 7.5 Hz,1H),7.13 (s,1H). [CD₃SOCD₃] |
| 2 | BOCNH (trans) | 3150,1700, 1630,1600, dp 165∼167° C. | 1.49(s,9H),3.41(d,J = 7.5 Hz,2H),6.89(t,J = 7.5 Hz,1H),7.08 (s,1H). [CD₃SOCD₃] |
| 3 | CbzNH | 3200,1738, 1715,1690, dp 169∼172° C. | 3.44,3.50,(2 × d,J = 8 Hz,2H),5.25(s,2H),7.07,7.35(2 × t,J = 8 Hz,1H),7.12(s,1H),7.38(brs,5H). [CDCl₃ + CD₃OD] |
| 4 | HCONH | 3400,1718, 1690,1630, 1550. dp 168° C. | 3.45,3.63(2 × d,J = 7.5 Hz,2H),7.14,7.32(2 × t,J = 7.5 Hz,1H), 7.23,7.25(2 × s,1H),8.51(s,1H). [CDCl₃ + CD₃OD] |

TABLE 8

Physical constants of 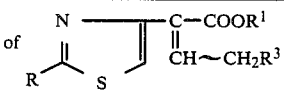

| No. | R | R¹ | R³ | IR(CHCl₃)ν:cm⁻¹ | NMR(CDCl₃)δ:ppm |
|---|---|---|---|---|---|
| 1 | BOCNH (anti-isomer) | Me | COOMe | 3415,1720 1541,1155. | 1.52(s,9H),3.54(d,J = 6.5 Hz,2H),3.64(s,3H), 3.76(s,3H),7.11(s,1H),7.18(t,1H),9.12(brs, 1H). |
| 2 | BOCNH (syn-isomer) | Me | COOMe | 3410,1720, 1541,1150. | 1.51(s,9H),3.54(d,J = 6.5 Hz,2H),3.69(s,3H), 3.83(s,3H),7.03(s,1H),7.08(t,J = 6.5 Hz,1H), 9.12(brs,1H). |
| 3 | CbzNH | Me | COOMe | nd. | 3.41,3.48(2 × d,J = 8 Hz,2H),3.65,3.73,3.69,3.83 (4 × s,6H),5.24(s,2H),7.00∼7.37(m,7H). |

TABLE 8-continued

Physical constants of 
$$\underset{R}{\overset{N}{\bigsqcup}}\underset{S}{\overset{}{\bigsqcup}}\overset{C-COOR^1}{\underset{CH-CH_2R^3}{\|}}$$

| No. | R | R$^1$ | R$^3$ | IR(CHCl$_3$)ν:cm$^{-1}$ | NMR(CDCl$_3$)δ:ppm |
|---|---|---|---|---|---|
| 4 | CbzNH | Et | COOEt | 3395,1720. | 1.19,1.20,1.22,1.30(4 × t,J = 8 Hz,6H),3.34,3.42 (2 × d,J = 8 Hz,2H),4.08,4.12,4.15,4.24(4 × q,J = 8 Hz,4H),5.21,5.22,5.24(3 × s,2H),7.03,7.13(2 × t,J = 8 Hz,1H),7.03(s,1H),7.31(s,5H),10.15(brs, 1H). |
| 5 | CbzNH | CH$_2$Ph | COOCH$_2$Ph | 3400,1725. | 3.31,3.42(2 × d,J = 7 Hz,2H),5.01,5.03,5.11,5.17 (4 × s,6H),6.96~7.30(m,17H),10.19(brs,1H). |
| 6 | CbzNH | CHPh$_2$ | COOCH$_2$Ph | 3490,1725. | 3.34,3.40(2 × d,J = 7 Hz,2H),5.02,5.05,5.09,5.17 (4 × s,4H),6.8~7.4(m,23H),9.90(brs,1H). |
| 7 | CbzNH | Me | CN | — | 3.73,3.83(2 × s,3H),5.23,5.25(2 × s,3H),6.78 (t,J = 7 Hz,1H),7.12,7.23(2 × s,1H),7.35(s, 5H),9.82(brs,1H). |
| 8 | HCONH | Me | CN | 3310,2240, 1712,1695sh (Nujol) | 3.80,3.89(2 × s,3H),6.85,6.90(2 × t,J = 7 Hz,1H), 7.32,7.51(2 × s,1H),8.65(s,1H),11.15(brs, 1H). [CD$_3$COCD$_3$] |
| 9 | HCONH | Me (anti-isomer) | COOMe | — mp. 100° C. | 3.46(t,J = 7.5 Hz,2H),3.66(s,3H),3.78(s,3H), 7.05(s,1H),7.24(t,J = 7.5 Hz,1H),8.49(s,1H). |
| 10 | HCONH | Me (syn-isomer) | COOMe | — | 3.56(d,J = 7.0 Hz,2H),3.73(s,3H),3.84(s,3H), 7.02(t,J = 7 Hz,1H),7.12(s,1H),8.55(s,1H). |
| 11 | ClCH$_2$CONH | Me (anti-isomer) | COOMe | — | 3.50(d,J = 6.5 Hz,2H),3.68(s,3H),3.79(s,3H), 4.25(s,2H),7.24(s,1H),7.24(t,1H). |
| 12 | ClCH$_2$CONH | Me (syn-isomer) | COOMe | — | 3.60(d,J = 7 Hz,2H),3.75(s,3H),3.87(s,3H), 4.27(s, 2H), 7.18(s, 1H), 7.18(t,J = 7Hz,1H). |

What we claim is:

1. A process for producing a glutaconic acid compound by a condensation reaction of a thiazoleacetic acid compound (I) and an alkoxyacrylic acid compound (II) in the presence of a base, which comprises treating a thiazoleacetic acid compound (I) with a base selected from a hydride or lower alkoxide of an alkali metal to produce a carbanion (Ia), mixing this carbanion with an alkoxyacrylic acid compound (II) to produce an alkoxyglutaric acid compound (Ib), eliminating the alcohol R$^4$OH from the latter compound (Ib) to produce a glutaconic acid compound (III), and optionally hydrolysing the glutaconic acid compound (III) to produce free glutaconic acid compound (IV), said reaction being carried out in the presence of a solvent at a temperature of from −30° C. to 100° C. for 5 minutes to 10 hours, and wherein 1 to 3 equivalents of said alkoxyacrylic acid compound (II) is treated with said thiazoleacetic acid compound (I) in the presence of 2 to 5 molar equivalent of said base in 3 to 20 parts by weight of said solvent, said compounds (I), (Ia), (Ib), (II), (III) and (IV) having the formulas:

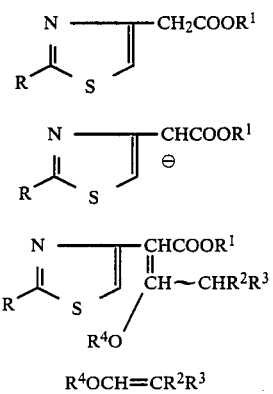

wherein,

R is amino or amino substituted by 1C to 5C alkanoyl, halo-1C to 5C-alkanoyl, 2C to 6C alkoxyformyl, 8C to 15C aralkoxyformyl, or 3C to 8C akylidene or aralkylidene;

R$^1$ is 1C to 8C alkyl, 1C to 5C haloalkyl, 1C to 5C akoxyalkyl, 1C to 8C sufonylalkyl, 2C to 5C alkenyl, or 7C to 15C aralkyl;

R$^2$ is hydrogen, cyano, or carboxy esterified by 1C to 8C alkyl, 1C to 5C haloakyl, 1C to 5C akoxyalkyl, 1C to 8C sulfonylalkyl, 2C to 5C alkenyl, or 7C to 15C aralkyl;

R$^3$ is hydrogen, cyano, or carboxy esterified by 1C to 8C alkyl, 1C to 5C haloalkyl, 1C to 5C akoxyalkyl, 1C to 8C sulfonylalkyl, 2C to 5C alkenyl, or 7C to 15C aralkyl; and R$^4$ is 1C to 5C alkyl or 7C to 15C aralkyl.

2. A process as claimed in claim 1 wherein the thiazoleacetic acid compound, alkoxyacrylic acid compound, and base are mixed together to produce the glutaconic acid compound.

3. A process as claimed in claim 1 wherein R$^3$ is hydrogen.

4. A process as claimed in claim 1 wherein the process is carried out in a solvent selected from a hydrocarbon, ether, nitrile, sulfoxide, amide, or ester solvent or a mixture thereof.

5. A process as claimed in claim 1 wherein an alkoxyacrylic acid compound is used as a reaction solvent.

6. A process as claimed in claim 1 wherein the product (III) is hydrolyzed to produce a glutaconic acid compound (IV).

7. A process according to claim 1 in which the alkoxyglutaric acid compound (b) is isolated from the reaction mixture prior to the elimination of the alcohol R$^4$OH therefrom.

* * * * *